United States Patent
Zanin et al.

(10) Patent No.: US 11,116,480 B2
(45) Date of Patent: Sep. 14, 2021

(54) IMAGE GUIDED STEERING OF A TRANSDUCER ARRAY AND/OR AN INSTRUMENT

(71) Applicant: Analogic Corporation, Peabody, MA (US)

(72) Inventors: Eric Francis Zanin, Lexington, MA (US); Spiros Mantzavinos, Lynn, MA (US); Ram Naidu, Newton, MA (US)

(73) Assignee: BK Medical Holding Company, Inc., Peabody, MA (US)

(*) Notice: Subject to any disclaimer, the term of this patent is extended or adjusted under 35 U.S.C. 154(b) by 657 days.

(21) Appl. No.: 15/569,534

(22) PCT Filed: Apr. 28, 2015

(86) PCT No.: PCT/US2015/027915
§ 371 (c)(1),
(2) Date: Oct. 26, 2017

(87) PCT Pub. No.: WO2016/175758
PCT Pub. Date: Nov. 3, 2016

(65) Prior Publication Data
US 2018/0303463 A1    Oct. 25, 2018

(51) Int. Cl.
*A61B 8/08*    (2006.01)
*A61B 8/00*    (2006.01)
(Continued)

(52) U.S. Cl.
CPC .......... *A61B 8/5223* (2013.01); *A61B 8/0841* (2013.01); *A61B 8/4466* (2013.01);
(Continued)

(58) Field of Classification Search
None
See application file for complete search history.

(56) References Cited

U.S. PATENT DOCUMENTS

| 9,558,405 B2* | 1/2017 | Leong | G06K 9/00624 |
| 2010/0010348 A1* | 1/2010 | Halmann | A61B 8/42 600/443 |

(Continued)

FOREIGN PATENT DOCUMENTS

WO    2014087324 A1    6/2014

OTHER PUBLICATIONS

International Search Report for PCT/US20151027915 published as WO2016/175758 dated Nov. 3, 2016.
(Continued)

*Primary Examiner* — Joanne M Hoffman
(74) *Attorney, Agent, or Firm* — Anthony M. Del Zoppo, III; Daugherty & Del Zoppo, Co, LPA

(57) ABSTRACT

A method includes registering a region of interest in 3-D imaging data with an initial ultrasound image so that the region of interest is in an imaging plane of the initial ultrasound image. The method further includes acquiring a subsequent ultrasound image with a transducer array. The method further includes comparing the initial ultrasound image and the subsequent ultrasound image. The method further includes steering at least one of the transducer array or an instrument based on a result of the comparing so that at least one of the region of interest or the instrument is in the imaging plane.

18 Claims, 6 Drawing Sheets

(51) Int. Cl.
*A61B 5/055* (2006.01)
*A61B 6/00* (2006.01)
*A61B 8/12* (2006.01)

(52) U.S. Cl.
CPC ............ *A61B 8/4488* (2013.01); *A61B 8/469* (2013.01); *A61B 8/5246* (2013.01); *A61B 8/54* (2013.01); *A61B 5/055* (2013.01); *A61B 6/5235* (2013.01); *A61B 8/12* (2013.01); *A61B 8/4218* (2013.01); *A61B 8/4461* (2013.01); *A61B 8/483* (2013.01); *A61B 8/5261* (2013.01)

(56) References Cited

U.S. PATENT DOCUMENTS

| | | | |
|---|---|---|---|
| 2010/0069756 A1* | 3/2010 | Ogasawara | G01S 7/52039 600/447 |
| 2012/0116219 A1* | 5/2012 | Miller | A61B 8/485 600/438 |
| 2012/0226145 A1* | 9/2012 | Chang | A61B 34/72 600/424 |
| 2014/0187946 A1* | 7/2014 | Miller | A61B 8/54 600/440 |
| 2014/0236001 A1* | 8/2014 | Kondou | A61B 8/4254 600/424 |
| 2014/0316247 A1* | 10/2014 | Hwang | A61N 7/02 600/411 |
| 2015/0359512 A1* | 12/2015 | Boctor | A61B 8/469 600/444 |
| 2016/0045186 A1* | 2/2016 | Cong | A61B 8/463 600/440 |
| 2016/0058424 A1* | 3/2016 | Fialkov | A61B 8/468 600/411 |
| 2017/0079623 A1* | 3/2017 | Kruecker | A61B 5/066 |
| 2017/0164931 A1* | 6/2017 | Ng | A61B 8/0841 |
| 2018/0146955 A1* | 5/2018 | Kruecker | A61B 8/4245 |
| 2018/0153619 A1* | 6/2018 | Kustra | A61N 7/02 |
| 2019/0209130 A1* | 7/2019 | Lieblich | A61B 8/463 |

OTHER PUBLICATIONS

P. Abolmaesumi, et al., Image-guided control of a robot for medical ultrasound, IEEE Trans.on Robotics and Automation, Jan. 1, 2002.
Ott L, et al. Robotic Assistance to Flexible Endoscopy by Physiological-Motion Tracking, IEEE Trans.on Robotics Service Center, Apr. 1, 2011.

* cited by examiner

IMAGE GUIDED STEERING OF A TRANSDUCER ARRAY AND/OR AN INSTRUMENT

RELATED APPLICATION

This application is a national filing of PCT application Ser. No. PCT/US2015/027915, filed Apr. 28, 2015, published as W02016/175758 on Nov. 3, 2016. This application claims priority to PCT application Ser. No. PCT/US2015/027915, published as W02016/175758 on Nov. 3, 2016.

TECHNICAL FIELD

The following generally relates to imaging and more particularly to steering a transducer array and/or an instrument based on a region of interest in imaging data, and is described with particular application to ultrasound imaging data, but is also amenable to imaging data generated by other imaging modalities.

BACKGROUND

An ultrasound (US) imaging system includes a transducer array that transmits an ultrasound beam into an examination field of view. As the beam traverses structure (e.g., of a sub-region of an object or subject) in the field of view, sub-portions of the beam are attenuated, scattered, and/or reflected off the structure, with some of the reflections (echoes) traversing back towards the transducer array. The transducer array receives the echoes. In B-mode imaging, the echoes are processed (e.g., delayed, weighted and summed) to generate scanlines, which are subsequently converted based on a display monitor format and displayed as an image via the display monitor.

Ultrasound imaging has been used in a wide range of medical and non-medical procedures. Examples of such procedures include surgery, biopsy, therapy, etc. In general, ultrasound images lack the quality of other imaging modalities in the level of diagnostic information. Magnetic resonance imaging (MRI) images and/or computed tomography (CT) images have higher diagnostic quality, but MRI and CT images can be difficult to acquire in real time during certain procedures. In contrast, ultrasound images are relatively easily acquired in real time during procedures. Fusion of a pre-procedure MRI and/or CT image and an intra-operative US image data leverages the high image quality of the MRI and/or CT image data and the real-time imaging capability of US.

Transducer plane position has been determined by the operator's subjective interpretation of the reconstructed image on the ultrasound display relative to known anatomical features. Unfortunately, this can lead to inaccurate positioning and/or repeat positioning. Patient movement, surgical manipulations and deformations caused by measuring devices modify the imaged organ such that regions of interest move relative to the pre-procedure plan. Unfortunately, the transducer may have to be re-positioned every time the region of interest moves relative to the imaging plane. With a prostate biopsy, a transrectal probe often has to be manually rotated to sweep regions of interest and follow needle movements. From the foregoing, positioning an imaging transducer and/or instrument in certain procedures can be challenging and time consuming.

SUMMARY

Aspects of the application address the above matters, and others.

In one aspect, a method includes registering a region of interest in 3-D imaging data with an initial ultrasound image so that the region of interest is in an imaging plane of the initial ultrasound image. The method further includes acquiring a subsequent ultrasound image with a transducer array. The method further includes comparing the initial ultrasound image and the subsequent ultrasound image. The method further includes steering at least one of the transducer array or an instrument based on a result of the comparing so that at least one of the region of interest or the instrument is in the imaging plane.

In another aspect, a system includes an ultrasound imaging apparatus with a transducer array. The system further includes a memory with computer executable instructions, the computer executable instructions including an auto-lock and guide mode, a registration algorithm, a tracking algorithm, and a correction algorithm. The system further includes a processor configured to execute the computer executable instructions in response to activation of the auto-lock and guide mode, wherein the processor, in response to executing the computer executable instructions, steers at least one of the transducer array or an instrument based on the registration, tracking, and correction algorithms so that at least one of a region of interest or the instrument is in an imaging plane of images generated by the ultrasound imaging apparatus during a procedure.

In another aspect, a computer readable storage medium is encoded with computer executable instructions, which, when executed by a processor, causes the processor to: obtain a procedure plan, which 3-D imaging data with a boundary of a region of interest marked therein, load the procedure plan, obtain an ultrasound image, identify the region of interest in an imaging plane of the ultrasound image based on the region of interest in the 3-D imaging data, acquire a subsequent ultrasound image, determine a difference in position of the region of interest in the ultrasound image and the region of interest in the subsequent ultrasound image, and control at least one of the transducer array or an instrument based on the difference to maintain the region of interest or the instrument is in the imaging plane.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
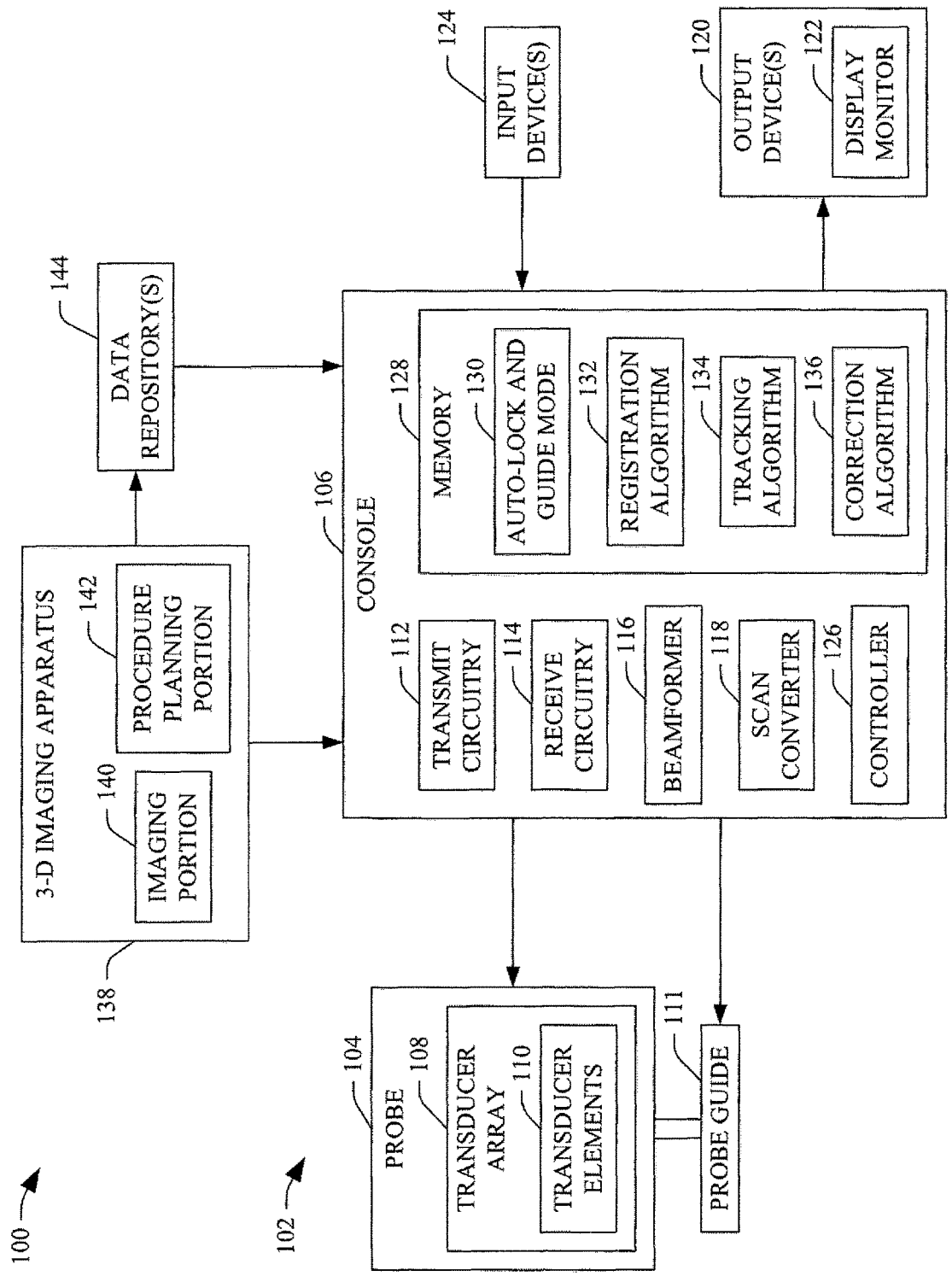
FIG. 1 schematically illustrates an example system.

FIG. 1 illustrates a system 100.

The system 100 includes an US imaging apparatus 102 with a probe 104 and a console 106. The probe 104 includes a 1-D (one-dimensional), 2-D (two-dimensional), or 3-D (three-dimensional) transducer array 108 with one or more transducer elements 110. The transducer array 108 can be linear, curved, and/or otherwise shaped, fully populated, sparse and/or a combination thereof, etc. The transducer elements 110 are configured to transmit ultrasound signals and receive echo signals. As described in greater detail below, in one instance, the transducer array 108 is at least one of electronically and/or mechanically steerable, automatically and/or manually.

The system 100 further includes a probe guide 111. The probe guide 111 is configured to support the probe 104 at least during a procedure. In one instance, the probe guide 111 holds the transducer array 108 at a static position, and the transducer array 108 is electronically and/or mechanically steered. In another instance, the probe guide 111 is alternatively and/or additionally moveable, and is used to electronically and/or mechanically steer the transducer array 108, automatically (e.g., via a motor, etc.) and/or manually (e.g., by a user, a robot, etc.). In yet another embodiment, the probe guide 111 is omitted and the probe 104 is held by a user.

The console 106 includes transmit circuitry 112 configured to excite one or more of the transducer elements 110, e.g., through a set of pulses (or a pulsed signal) that is conveyed to the transducer array 108, which causes the one or more of the transducer elements 110 to transmit ultrasound signals. The console 106 further includes receive circuitry 114 configured to receive echoes (RF signals) generated in response to the transmitted ultrasound signals from the transducer array 108. The echoes, generally, are a result of an interaction between the emitted ultrasound signals and structure (e.g., flowing blood cells, organ cells, etc.) in the scan field of view.

The console 106 further includes a beamformer 116 configured to process the received echoes. In B-mode, this includes applying time delays and weights to the echoes and summing the delayed and weighted echoes. The beamformer 116 may be further configured for spatial compounding, filtering (e.g., FIR and/or IIR), and/or other echo processing. The console 106 further includes a scan converter 118 configured to convert the beamformed data for display via a display monitor 122. The console 106 further includes an output device(s) 120, including the display monitor 122. The console 106 further includes an input device(s) 124, including a keyboard, a mouse, a trackball, a touchpad, a touchscreen, knobs, buttons, sliders, and/or other input device.

The console 106 further includes a controller 126 and non-transitory computer readable medium ("memory") 128, which excludes transitory computer readable medium such as signals, carrier mediums, etc. The controller 126 is configured to execute one or more instructions embedded, encoded, stored, etc. in the memory 128. In this example, the memory 128 at least stores an auto-lock and guide mode 130, a registration algorithm 132, a tracking algorithm 134, and a correction algorithm 136. The mode 130 can be activated and deactivated, e.g., via a user actuating the input device(s) 124. In response thereto, the controller 126 executes the registration algorithm 132, the tracking algorithm 134, and the correction algorithm 136.

The registration algorithm 132 includes instructions for registering a region of interest (e.g., anatomical tissue of interest) identified in received 3-D reference planning image data with an imaging plane in a reference real-time ultrasound image. A non-limiting example of a suitable registration is described in international application serial number PCT/US13/72154, filed on Nov. 27, 2013, and entitled "Multi-Imaging Modality Navigation System," the entirety of which is incorporated herein by reference. PCT/US13/72154 describes an approach in which a location and a spatial orientation of a 2-D ultrasound slice is located and/or mapped to a corresponding plane in a 3D volume. Other approaches are contemplated herein.

The tracking algorithm 134 tracks the region of interest in newly acquired real-time ultrasound image to the region of interest in the reference previously acquired ultrasound image. Miss-alignment between the regions of interest between frames may be due to movement of a scanned object, the region of interest, the probe 104, etc. The correction algorithm 136 generates a position correction signal based on a location and/or position difference between the regions of interest. An example correction signal, e.g., may indicate the imaging plane needs to move to the left two millimeters (2 mm) to align the regions of interest.

The controller 126 is further configured to control various components of the system 100, such as the transmit circuitry 112 and/or the probe guide 111. In one instance, the controller 126, based on the position correction signal, controls the transmit circuitry 112 and/or probe guide 111 to steer the imaging plane to align the regions of interest. The frequency of such control can be every frame, every other frame, every third frame, an irregular interval, on demand, based on a predetermined frequency, etc. Continuing with the above example, the correction signal may result in the probe 104 being moved to the left two millimeters.

Alternatively and/or additionally, the controller 126, based on the position correction signal, displays a message on the display monitor 122. In one instance, the message includes alphanumeric characters in human readable format that indicates the user should move the probe 104 (e.g., "please move the probe to the left 2 millimeters). In another embodiment, the message could include graphics. For example, the message could include arrows pointing in a direction of movement, color or gray scale that indicates the movement, etc.

The system 100 further includes a 3-D imaging apparatus 138 with an imaging portion 140, which includes one or more of ultrasound (US), magnetic resonance (MR), computed tomography (CT), single photon emission computed tomography (SPECT), positron emission tomography (PET), X-ray, and/or other imaging modality. The 3-D imaging apparatus 138 generates the 3-D reference planning image data. The 3-D imaging apparatus 138 further includes a procedure planning portion 142, which identifies the region of interest in the 3-D reference planning image data using an automatic, semi-automatic, and/or manual approach. In one instance, this includes marking and/or otherwise identifying the boundary, the perimeter, and/or other landmark of the region of interest.

The illustrated system 100 further includes a data repository 144 configured to store imaging data and/or other data. In this example, the data repository 144 can store the 3-D reference planning image data, the region of interest and/or a procedure plan. Examples of data repositories include a picture archiving and communication system (PACS), a radiology information system (RIS), a hospital information system (HIS), an electronic medical record (EMR), etc. The console 106 can receive and/or retrieve the 3-D reference planning image data with the region of interest from the data repository 144.

It is to be appreciated that the real-time active steering process disclosed herein enables a workflow improvement through at least one of accuracy and speed improvements. In general, the mode 130 and algorithms 132-138 can be regarded as an image-guided automated positioning system (iGAP). The iGAP allows the transducer array 108 to be dynamically guided, e.g., during a biopsy, surgical, treatment and/or other application, based on a region of interest identified in a pre-procedure image, such as an MRI, a CT, etc. image.

Figure 2:
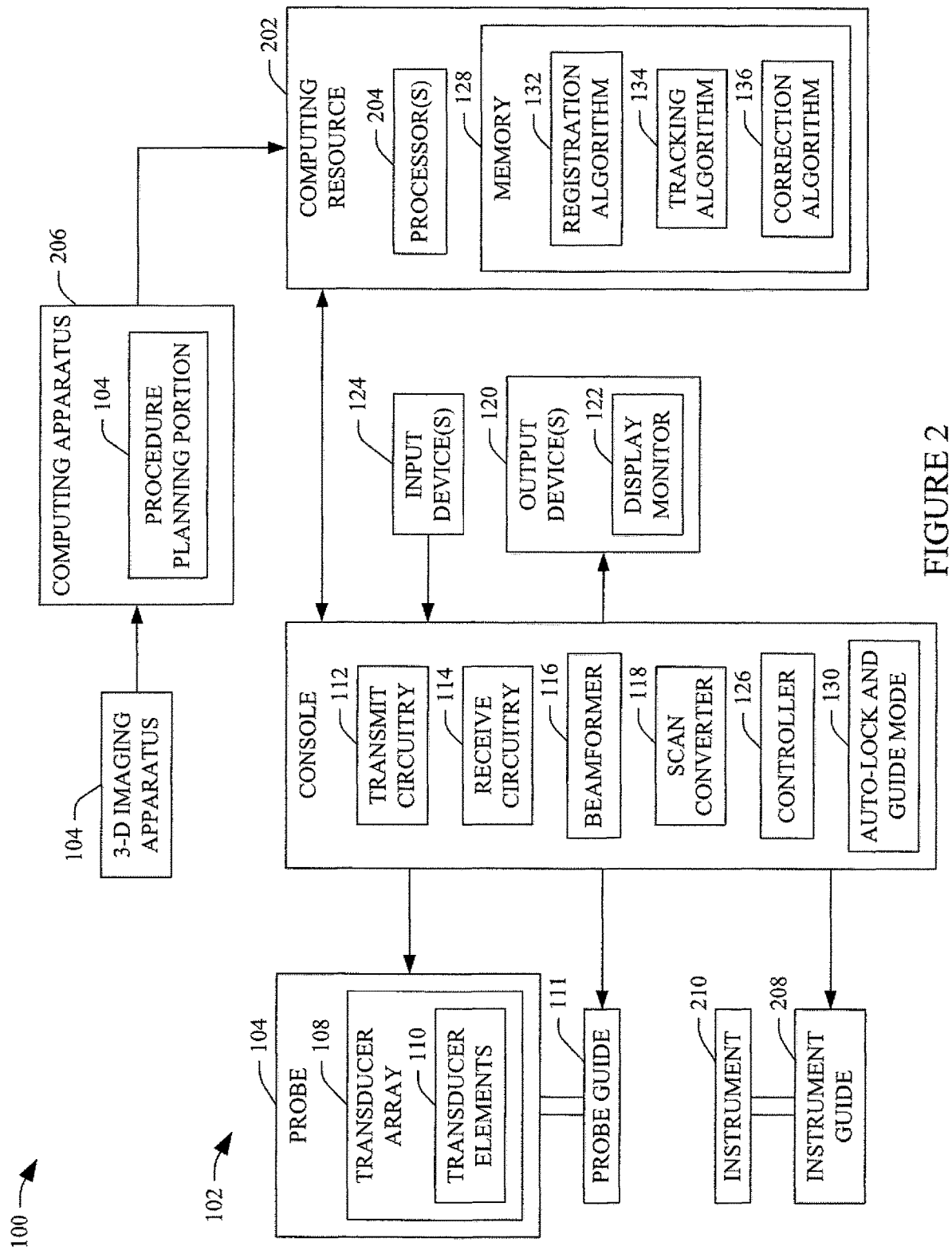
FIG. 2 schematically illustrates a variation of the example system of FIG. 1.

FIG. 2 schematically illustrates a variation of FIG. 1 in which the registration algorithm 132, the tracking algorithm 134, and the correction algorithm 136 are located and executed remotely from the console 106, e.g., via computing resources 202 such as a "cloud" based and/or other remote computing resource. The computing resources 202 include a processor(s) 204 such as one or more microprocessor, central processing units, and/or other processors. This example also includes a computing apparatus 206, and the procedure planning portion 142 is located in the computing apparatus 206 instead of the 3-D imaging apparatus 102.

FIG. 2 further includes an instrument guide 208. The instrument guide 208 supports an instrument 210 such as a biopsy needle and/or other device. The instrument guide 208, in one instance, is similar to the probe guide 111 in that it can be used to steer the instrument 210, automatically (e.g., via a motor, etc.) and/or manually (e.g., by a user, a robot, etc.), to provide a guide to the region of interest, confirm the region of interest has been reached, record a biopsy, etc. Other variations include a combination of FIGS. 1 and 2 and/or other configuration.

Figure 3:
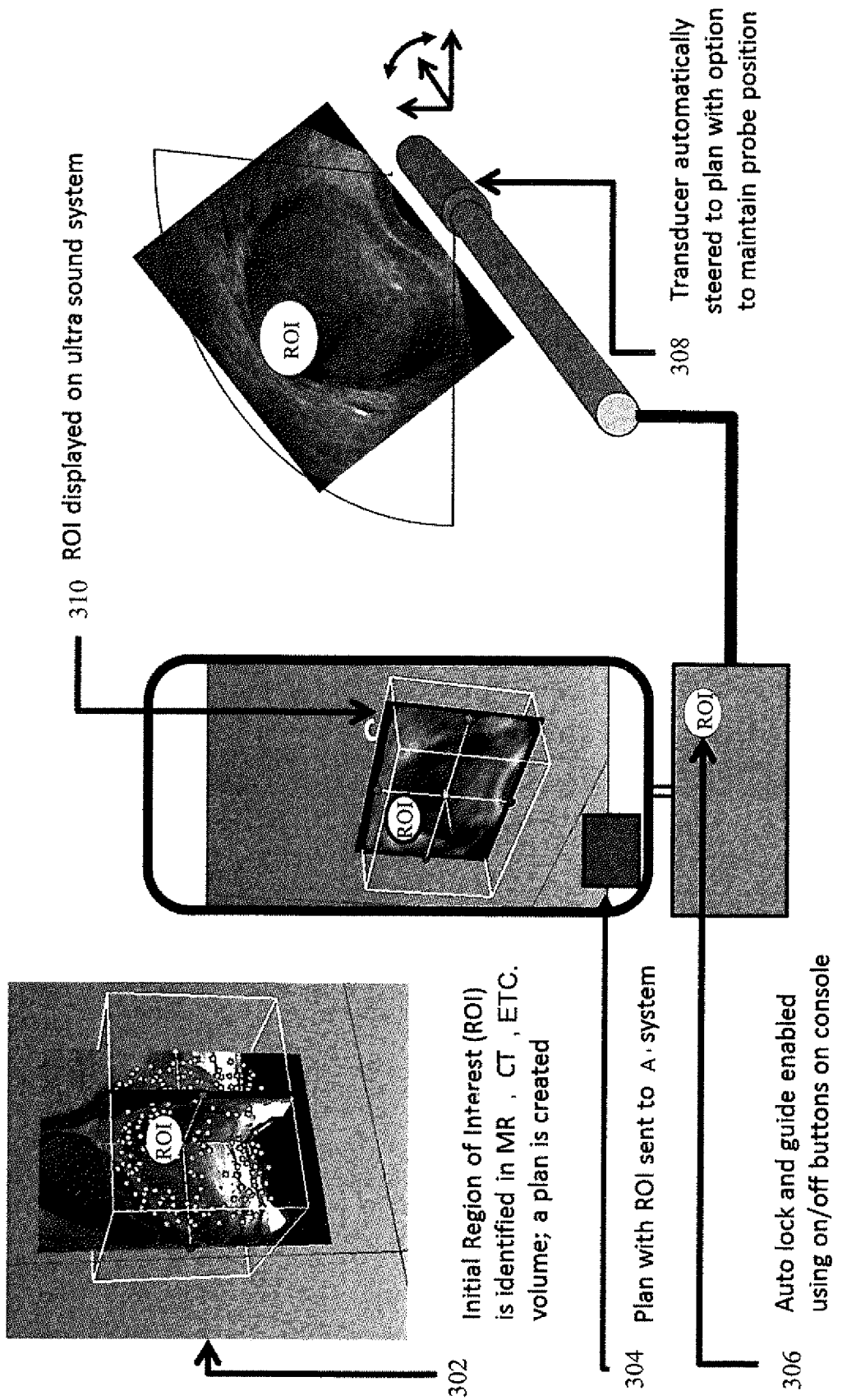
FIG. 3 illustrates example workflow.

FIG. 3 illustrates example workflow in accordance with one or more embodiments herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 302, a region of interest ("ROI") is identified in pre-procedure 3-D imaging data and a plan is created.

At 304, the plan with the ROI is loaded on the ultrasound system 102, the computing resource 202, and/or other machine(s) running the algorithms 132-136.

At 306, the system activates auto-lock and guide mode, e.g., in response to receiving an input indicative of a user request to activate active-contour lock.

At 308, the algorithms 132-136 are executed to steer the transducer array 108 (and/or the instrument guide 208) so that the image plane in a newly acquired real time includes the region of interest (and/or the instrument 210) for each real time image.

At 310, the real-time US image and the ROI are both displayed.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

Figure 4:
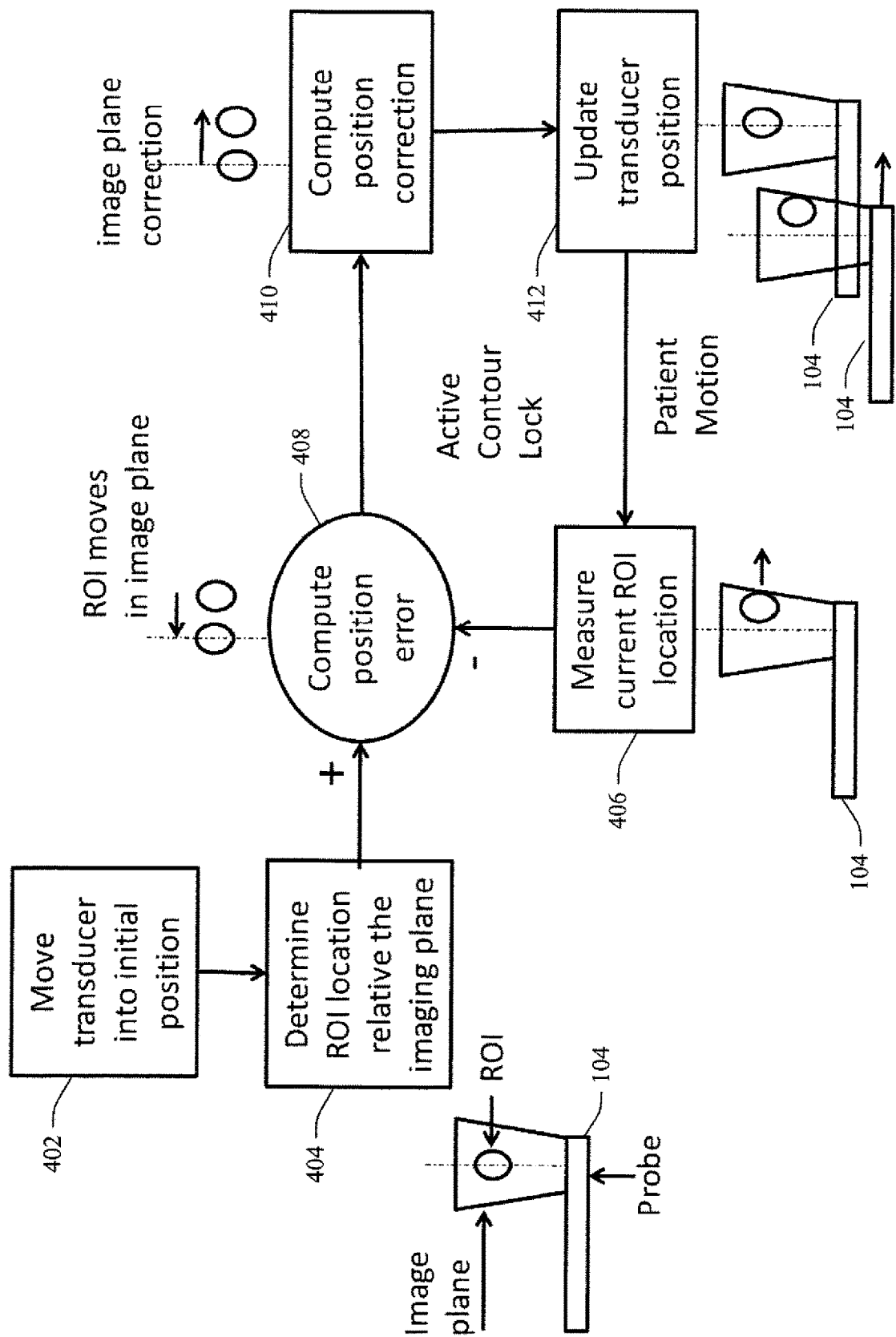
FIG. 4 illustrates an example.

FIG. 4 illustrates an example of act 308 of FIG. 3.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 402, the transducer 108 is moved to an initial position.

At 404, the ROI location is determined relative to the imaging plane.

Subsequently, the ROI is displaced from the imaging plane, for example, due to subject movement, ROI movement, probe 104 movement, etc.

At 406, a current location of the ROI is measured in a newly acquired real time US image.

At 408, a position error is computed as a difference between the location of the ROI relative to the imaging plane and the measured current ROI location.

At 410, a position correct signal is computed based on the position error.

At 412, the position correct signal is used to update the location of the transducer array 108 (and/or the instrument guide 208) so that the image plane in a newly acquired real time includes the region of interest (and/or the instrument 210) for each real time image.

Acts 406-412 are repeated for subsequently acquired real time US image so the ROI is always imaged at a fixed location within the imaging plane. The process can be repeated in a control loop to servo the device in real-time.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

FIGS. 5-10 schematically show non-limiting examples of the probe 104 and the transducer array 108.

Figure 5:
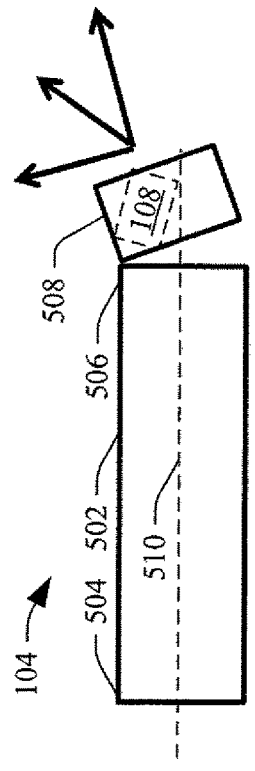
FIG. 5 shows an example probe with a moveable transducer array at a first position.
Figure 6:
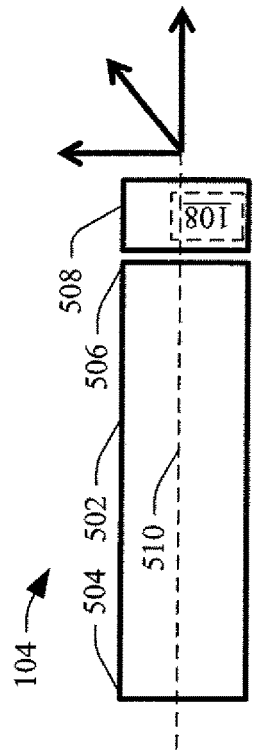
FIG. 6 shows an example of the probe of FIG. 5 with the moveable transducer array at a second position.

FIGS. 5 and 6 show a configuration in which the probe 104 includes an elongate region or handle 502, including a proximal end 504 and a distal end 506, and a second region or probe tip 508, which is moveably attached to the distal end 506. The transducer array 108 is disposed in the second region 508. The second region 508 is configured to deflect about a central axis 510. In this example, the second region 508 deflects in the x, y and/or z directions. FIG. 5 shows a straight second region 508. FIG. 6 shows a deflected second region 508.

Figure 7:
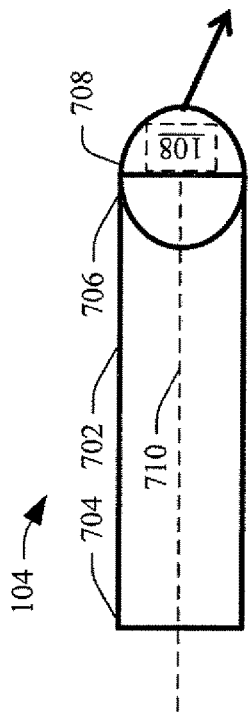
FIG. 7 shows an example probe with a rotatable transducer array at a first position.
Figure 8:
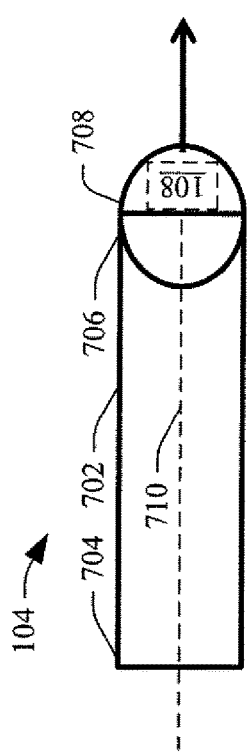
FIG. 8 shows an example of the probe of FIG. 7 with the rotatable transducer array at a second position.

FIGS. 7 and 8 show a configuration in which the probe 104 includes an elongate region or handle 702, including a proximal end 704 and a distal end 706, and a second region or probe tip 708, which is rotatably attached to the distal end 706. The transducer array 108 is disposed in the second region 708. The second region 708 is configured to rotate about a central axis 710. In this example, the second region 708 can rotate 360 degrees, more or less. FIG. 7 shows a straight non-rotated second region 708. FIG. 8 shows a rotated second region 708.

Figure 9:
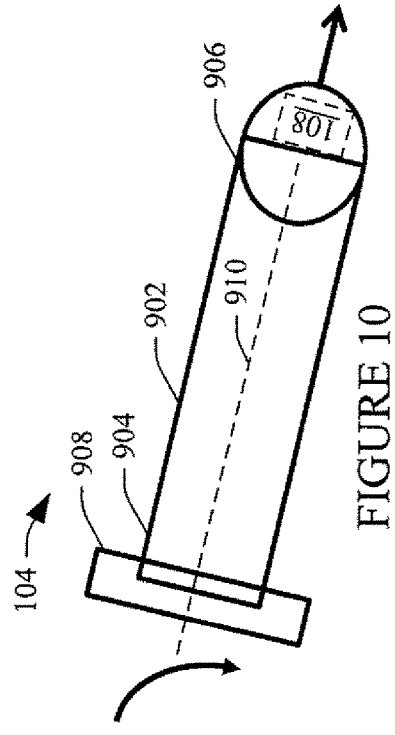
FIG. 9 shows an example probe with an articulating transducer array at a first position.
Figure 10:
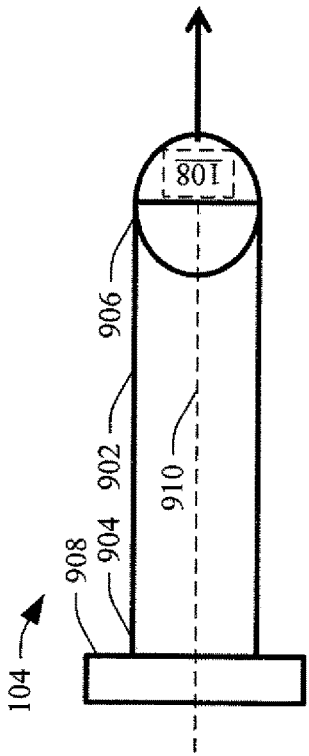
FIG. 10 shows an example of the probe of FIG. 9 with the articulating transducer array at a second position.

FIGS. 9 and 10 show a configuration in which the probe 104 includes an elongate region or handle 902, including a proximal end 904 and a distal end 906. The proximal end 904 is affixed to an articulating member 908, and the transducer array 108 is disposed at the distal end 906. The articulating member 906 is configured to articulate about a central axis 910. In this example, the articulating member 906 can articulate in the x, y and/or z directions. FIG. 9 shows the elongate region 902 extending along the central axis 910. FIG. 10 shows the elongate region 902 articulated.

In general, the above configurations include a mechanical means for steering the image plane. These means can be controlled electrically and automatically, and/or manually by an operator. Furthermore, the image plane can additionally be steered through selective excitation of the transducer elements 110 of the transducer array 108. It is also to be appreciated that another embodiment includes a combination of two or more of the embodiments depicted in FIGS. 5-10. One or more other embodiments are also contemplated herein.

Figure 11:
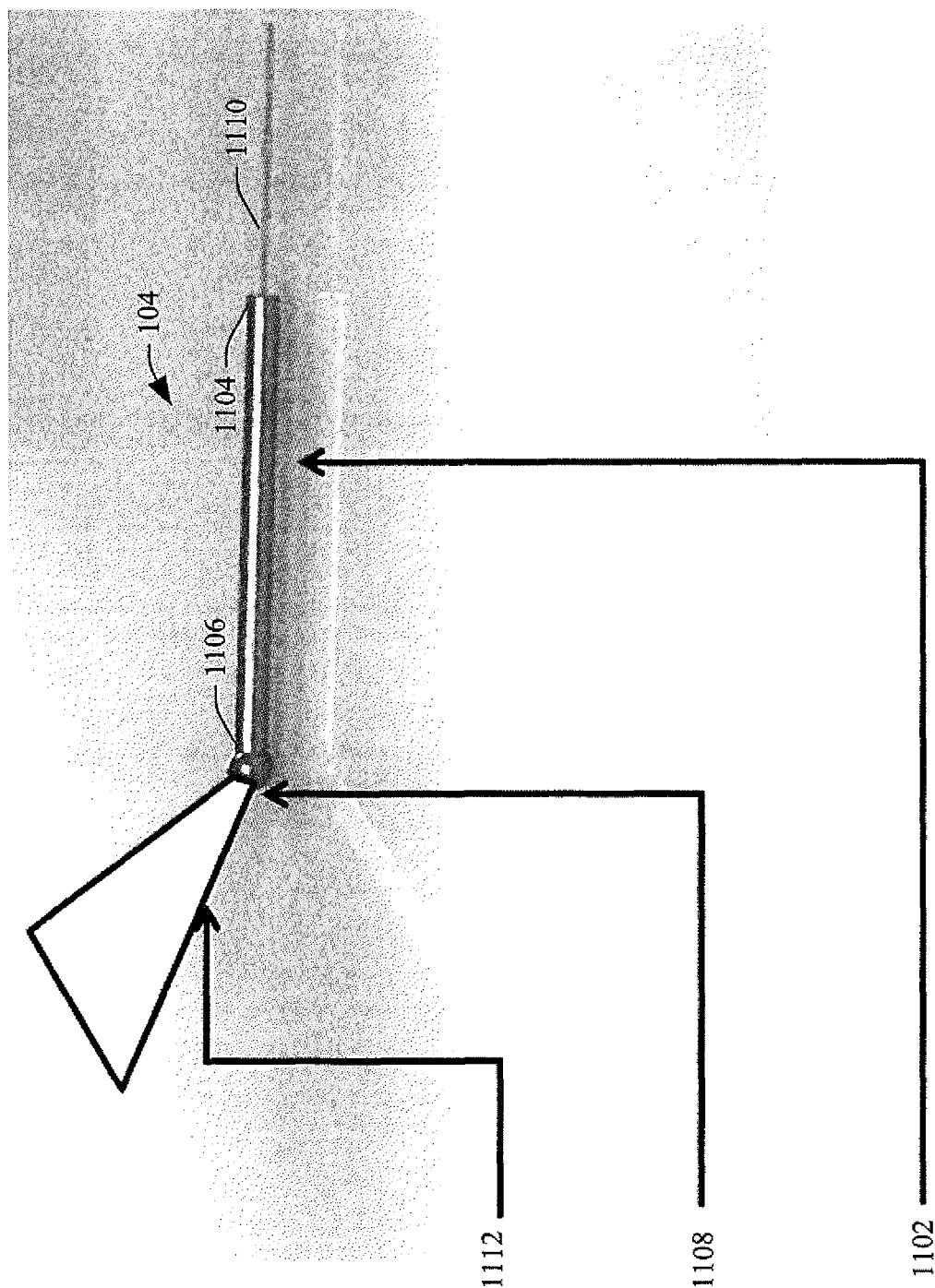
FIG. 11 shows another example probe.

For example, FIG. 11 shows a configuration in which the probe 104 includes an elongate region or handle 1102, including a proximal end 1104 and a distal end 1106, and a second region or probe tip 1108 attached thereto, e.g., through a ball-and-socket joint. The transducer array 108 (not visible) is disposed in the second region 1108. A conduit 1110 between the transducer elements 110 and the console 106 extends out of the proximal end 1104. An image plane 1112 is shown in connection with the transducer array 108. In another example, rotating is achieved synthetically by combining data generated by the transducer array 108.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method, comprising:
    identifying a region of interest in the 3-D image of a subject acquired prior to a procedure on the subject, wherein the region of interest includes an anatomical tissue of interest
    acquiring, with a transducer array of an ultrasound probe of an ultrasound imaging apparatus, a first ultrasound image of the subject during the procedure;
    registering the 3-D image with the first ultrasound image by registering the region of interest in the 3-D image with the first ultrasound image to find the region of interest in an imaging plane of the first ultrasound image;
    acquiring, with the transducer array of the ultrasound probe during the procedure and after acquiring the first ultrasound image, a second ultrasound image of the subject;
    identifying the region of interest in an imaging plane of the second ultrasound image;
    comparing a location of the region of interest in the imaging plane of the first ultrasound image and a location of the region of interest in the imaging plane of the second ultrasound image;
    determining, based on a result of the comparing, a difference between the location of the region of interest in the imaging plane of the first ultrasound image and the location of the region of interest in the imaging plane of the second ultrasound image; and
    steering, based on the difference, the transducer array so that a location of the region of interest in an imaging plane of a third ultrasound image of the subject acquired with the transducer array of the ultrasound probe during the procedure after acquiring the second ultrasound image spatially aligns with the location of the region of interest in the imaging plane of the first ultrasound image.

2. The method of claim 1,
    wherein the difference represents a position error, and further comprising:
    computing a position correction signal indicative of the position error; and
    steering the transducer array based on the position correction.

3. The method of claim 2, further comprising:
    acquiring the 3-D image with an imaging device.

4. The method of claim 3, wherein the imaging device includes at least one of a magnetic resonance imaging or a computed tomography scanner.

5. The method of claim 1, further comprising:
    controlling the steering of the transducer array with a processor of the ultrasound imaging apparatus; and
    performing all of the other acts with a processor external from the ultrasound imaging apparatus.

6. The method of claim 2, further comprising:
    performing all of the acts with the ultrasound imaging apparatus.

7. The method of claim 1, further comprising:
    electronically steering the transducer array.

8. The method of claim 1, further comprising:
    physically deflecting the transducer array to steer the transducer array.

9. The method of claim 1, further comprising:
    rotating the transducer array to steer the transducer array.

10. The method of claim 1, further comprising:
    articulating an articulating member affixed to the transducer array to steer the transducer array.

11. The method of claim 1, further comprising:
    manually moving the transducer array to steer the transducer array.

12. The method of claim 1, further comprising:
    controlling a probe guide to steer the transducer array, wherein the probe guide supports the transducer array.

13. The method of claim 1, further comprising:
    controlling an instrument guide to steer an instrument based on the difference, wherein the instrument guide supports the instrument.

14. The method of claim 13,
    wherein the instrument guide is steered so that it is in the imaging plane of each acquired ultrasound image.

15. The method of claim 1, further comprising:
    using the region of interest in 3-D image to create a plan;
    loading the plan into memory of a computing system;
    receiving an input that activates an auto-lock and guide mode; and
    automatically steering the transducer array.

16. The method of claim 1, further comprising:
    displaying a message on a display monitor based on the position correction signal.

17. The method of claim 16, wherein the message includes alphanumeric characters in human readable format instructing a user of the transducer array to move the transducer array by a fixed distance.

18. The method of claim 16, wherein the message includes a graphics that indicates a direction of movement of the transducer array.

* * * * *